United States Patent [19]

Schneider et al.

[11] 4,107,223
[45] Aug. 15, 1978

[54] PROCESS FOR IMPROVING THE LOW TEMPERATURE PROPERTIES OF TETRAHYDROALKYLDICYCLOPENTADI-ENES

[75] Inventors: Abraham Schneider, Overbrook Hills; Richard E. Ware, Aston, both of Pa.

[73] Assignee: Suntech, Inc., St. Davids, Pa.

[21] Appl. No.: 720,305

[22] Filed: Sep. 3, 1976

[51] Int. Cl.$^2$ .............................................. C07C 5/24
[52] U.S. Cl. ................................ 260/666 PY; 60/208
[58] Field of Search ................... 260/666 PY; 60/208, 60/211

[56] References Cited

U.S. PATENT DOCUMENTS 3,864,178   2/1975   Rudy et al. .................... 149/109.6 X Primary Examiner—Stephen J. Lechert, Jr.
Attorney, Agent, or Firm—J. Edward Hess; Donald R. Johnson; Anthony Potts, Jr.

[57] ABSTRACT

Endo-tetrahydroalkyldicyclopentadienes are mildly isomerized with AlCl$_3$ whereby the changes in pour point and viscosities are such that the resulting isomeric mixture can be used as a diluent for a higher viscosity hydrocarbon missile fuel. The isomerization is such that essentially no alkyl-adamantanes are formed. The mole ratio of AlCl$_3$ to the tetrahydrodienes is in the range from between about 0.001 to about 0.5. The temperature is in the range between from about 0° C to about 100° C.

9 Claims, No Drawings

PROCESS FOR IMPROVING THE LOW TEMPERATURE PROPERTIES OF TETRAHYDROALKYLDICYCLOPENTADIENES

The invention herein described was made in the course of or under a contract thereunder with the United States Air Force Systems Command.

CROSS REFERENCES TO RELATED APPLICATION

This application is related to the following applications filed same date:

| Serial No. | Inventors | Title |
|---|---|---|
| 720,306 | Edward J. Janoski, et al | Isomerization of Tetrahydropolycyclopentadienes to Missile Fuel Additive |
| 720,308 | Richard E. Ware, et al | Isomerization of Tetrahydrotricyclopentadienes to Missile Fuel |
| 720,307 | Abraham Schneider, et al | Isomerization of Endo-tetrahydrodicyclopentadiene to a Missile Fuel Diluent |

BACKGROUND OF THE INVENTION

This invention relates to the preparation of an isomeric mixture of tetrahydroalkyldicyclopentadienes, i.e. tetrahydrodimethyldicyclopentadiene and/or tetrahydromethyldicyclopentadiene. The latter is referred to hereinafter as THMeDCPD while the former THDMeDCPD. More particularly, the invention relates to the preparation of an isomeric mixture from endo-THDMeDCPD and/or endo-THMeDCPD. Still more particularly, the invention relates to the catalytic isomerization of endo-THDMeDCPD and/or THMeDCPD to an isomeric mixture.

The resulting isomeric mixture can be used as a diluent for higher viscosity, higher melting, high energy missile fuel. Thus it can be blended with such a fuel to lower its viscosity without adversely effecting its other properties. High energy fuel can be used in either jet or rocket propulsion. Jet propulsion includes a jet engine which can be used for missile, aircraft and others and includes the three basic types, i.e., ramjet, turbo-jet and pulse jet. The term rocket generally refers to a device containing its own oxygen or oxidizing agent. An article in Aviation Week and Space Technology, Jan. 26, 1976, pages 111–113, discloses some of the high density hydrocarbon fuels that have modified by the diluents disclosed herein.

U.S. Pat. No. 3,381,046 discloses the treatment of endo-THDMeDCPD, having a freezing point of −30° C, with sulfuric acid. The resulting hydrocarbon product had a freezing point below −80° C. It also discloses such treatment for endo-THMeDCPD. This patent also discloses generally that a Lewis acid, such as aluminum chloride, can be used to isomerize endo-THDMeDCPD, but cautions that the isomerization can proceed beyond the exo-diene to form alkyladamantanes.

SUMMARY OF THE INVENTION

Applicants isomerize liquid endo-THDMeDCPD, and/or endo-THMeDCPD using aluminum trichloride (AlCl$_3$) at a temperature and with a contacting time such that essentially no methyladamantanes are formed. An inert solvent is optional. Further, the isomerization is such that the resulting isomerized mixture has both a pour point and viscosity whereby it is suitable as a diluent for a higher viscosity, higher pour point missile fuel.

DESCRIPTION

The number of possible isomers of endo-THDMeDCP is large but to determine each isomer can be difficult. However, four of the major constituents of hydrogenated commercially available methylcyclopentadiene dimer have been isolated by preparative vapor phase chromotography and their structues determined by examinations involving infrared, mass and nuclear magnetic resonance spectroscopy. The structures of the four major components of increasing boiling points are throught to be as follows:

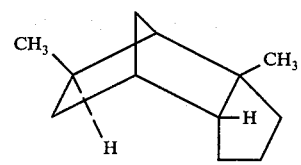
(I)

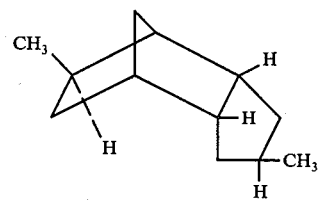
(II)

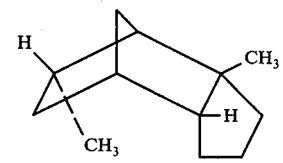
(III)

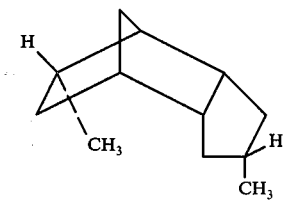
(IV)

The methyl groups in structure IV can be considered in the endo configuration whereas in structure I the methyls are in and exo configuration. The feed to applicants' method can be a mixture of any of the foregoing and/or other isomers as well as any individual isomer. With the other isomers the methyl groups would be attached to the structure at locations other than those shown. The feed can also be a monomethyltetrahydrodiene.

The isomerization of the endo-tetrahydromethyldine results, in part, in the conversion of the endo skeleton to the exo skeleton, and of the endo methyl groups to the exo configuration, thus:

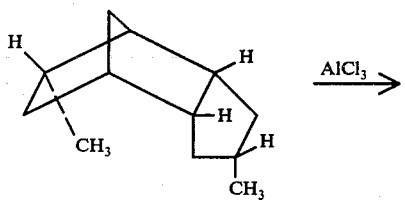

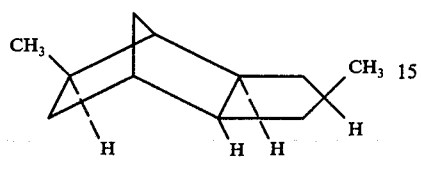

The feed to the process can also be an individual endo-THMeDCPD or a mixture of several isomers of endo-THMeDCPD. Attachment of the one methyl group give the following possible isomers:

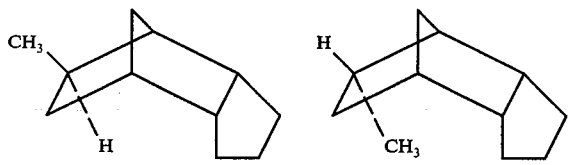

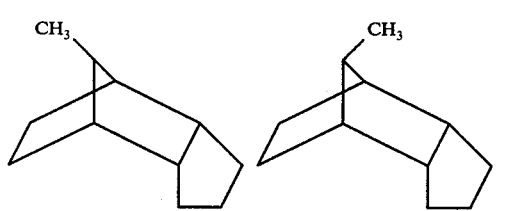

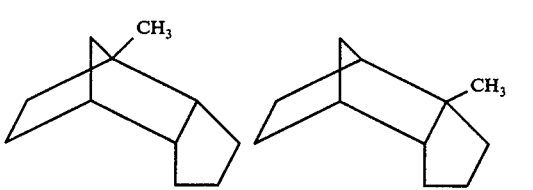

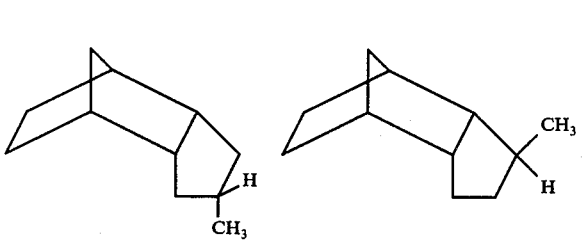

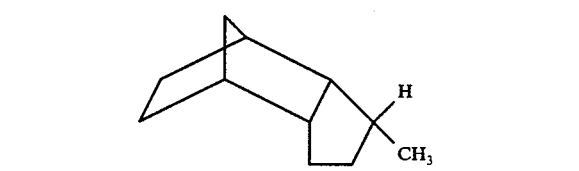

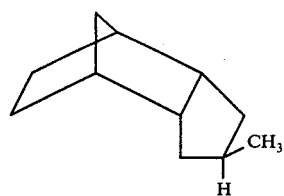

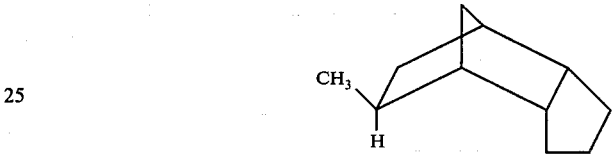

A methyl group in an endo configuration can be isomerized to an exo confirguration, thus:

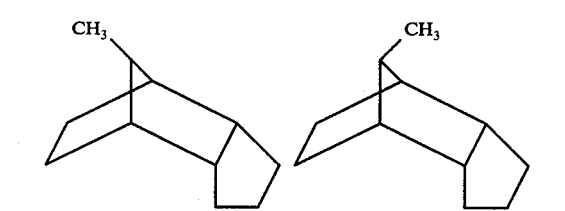

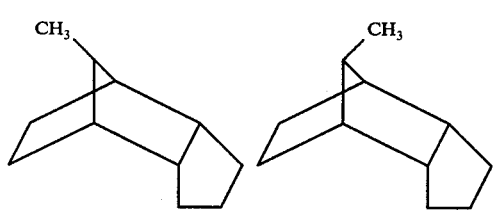

Thus as a result of the isomerization not only can the endo skeleton structure be change to the exo structure, but also the methyl groups can be changed from one form to another.

However, what is surprising, as shown by the data given in the examples, is that the isomerization can be controlled. Further, that by controlling the isomerization the production of undesirable products such as alkyladamantanes i.e., the dimethyls as well as the methyls, can be avoided. And still further, that by the controlled isomerization desired decreases in viscosities and pour points occur. Furthermore, that the aforementioned decreases are such that the resulting isomeric mixture can be used as a diluent for higher viscosity, high energy fuels.

The endo-THDMeDCPD and/or endo-THMeDCPD can contain other similar hydrocarbons. However, such hydrocarbons should not adversely affect the isomerization or the catalyst. Further, the similar hydrocarbon should not adversely influence the resulting properties of the isomerized tetrahydrodiene. Thus, for optimum results the feed consists essentially of endo-THDMeDCPD and/or endo-THMeDCPD.

The mole ratio of $AlCl_3$ to endo-THDMeDCPD and/or endo-THMeDCPD is such that the isomerization can be controlled. This control results in that essentially no alkyladamantanes are formed. Further, the isomerization is such that the resulting mixture of isomers has both a pour point and viscosity making it useful as a diluent for fuels for an air breathing missile. The mole ratio of $AlCl_3$ to the tetrahydroalkyldiene is in the range between from about 0.001 to about 0.5; a preferable range is between from about 0.01 to about 0.02.

The temperature of isomerization needs to be controlled between a narrow range. The lower limit can be influenced by the freezing point of the reaction mixture and/or the rate of the reaction. While the reaction can proceed at a very low temperature the rate could be so slow as to be commercially unattractive. Thus generally the lower temperature limit is about 0° C with about 10°

C preferred. The upper limit is controlled by the formation of undesirable products which adversely effect the properties of the resulting missile fuel. Also if the reaction rate is too rapid at an elevated temperature an uncontrolled exotherm could result. Thus generally the upper temperature limit is about 100° C with about 60° C preferred.

The pressure can vary substantially, however, economic consideration will favor a more limited range. Typically, the contacting will occur at atmospheric pressure. However, if a temperature is used which is greater than the boiling point of a solvent, if present, then it might be advantageous to use a higher pressure to prevent the solvent from boiling away.

An inert solvent can be used in the isomerization. Since the reaction is mildly exothermic the liquid solvent can serve as a heat sink. The solvent can also facilitate the handling of the contacting mixture and the resulting product. The inert solvent should not adversely react with the feed, product or $AlCl_3$. Suitable inert solvents include chlorinated paraffins such as methylene dichloride, tetrachloroethane, pentachloroethane and other similar materials. As to the amount of inert solvent used, excessive amounts can decrease the reaction rate and thus adversely effect the economics of a commercial operation.

The catalyst used for isomerization is anhydrous $AlCl_3$. Any material which could adversely affect its effectiveness during the isomerization should not be present. For example, the presence of hydroxylic compounds such as water, alcohol or oxygen from air could deactivate the $AlCl_3$.

Surprsingly, the isomerization can be controlled so that no alkyladamantanes are formed. The presence of alkyladamantanes would be a disadvantage because the density of alkyladamantanes are generally too low. In some instances freezing points are relatively too high, for example, 1,3-dimethyladamantane freezes at $-26°$ F. Such a co-product, i.e., one with a low density, as a diluent would excessively lower the density of the fuel and thereby result in a blend not meeting the density and energy requirements set for a missile fuel.

The isomeric tetrahydroalkyldiene resulting from the isomerization step has a kinematic viscosity and pour point which make it useful as a diluent for higher viscosity missile fuels. One such example of a higher viscosity missile fuel is the H-Binor-S missile fuel described in the aforementioned Aviation Week & Space Technology article. With a kinematic viscosity at 100° F of less than 4.01 cst and a pour point which is less than 0° F the isomeric tetrahydroalkyldiene is a desirable diluent. Of course the lower its viscosity the greater its usefulness as a diluent if its other properties do not change. In addition the isomeric tetrahydroalkyldiene has a density making it useful as a diluent for missile fuels. While the isomeric tetrahydroalkyldiene has a density less than 0.9216, a density much lower than 0.9079 could be undesirable. Thus the density is in the range between from 0.9216 to about 0.9079 with the higher densities preferred.

As indicated before, the resulting isomeric mixture can be one particular isomeric tetrahydroalkyldiene or a mixture of the tetrahydroalkyldiene isomers. It is probable, however, that the product would be a mixture of tetrahydroalkyldiene isomers because the cost of obtaining one particular tetrahydroalkyldiene as a starting material could be prohibitive.

To obtain an isomerized tetrahydroalkyldiene having a density, pour point and viscosity which make it useful as a diluent for a high density fuel, the reaction time or contacting time should be sufficient to obtain the desired properties. Sufficient time depends in part on the amount of tetrahydroalkyldiene isomerized, the amount of stirring, the amount of $AlCl_3$ used, the configuration of the vessel containing the reaction or contacting mixture, and other variables. Since the amount of isomerization can be monitored during the isomerization by measuring the viscosity, for example, when the desired amount of isomerization has been obtained, the reaction can be stopped.

After the reaction has been stopped the solvent, if any is used, can be removed. If the solvent has a relatively low boiling point it can be easily boiled off. After the solvent is removed the $AlCl_3$ and hydrocarbon tars, if any, can be easily separated, for example, by decantation. The tars and $AlCl_3$ together are often referred to as sludge. Some endo-tetrahydroalkyldienes can remain in the product without adversly effecting its usefulness. Aqueous washing of the isomeric tetrahydroalkyldiene mixture removes any remaining $AlCl_3$. Other means to recover the isomric tetrahydroalkyldiene from the solvent and sludge are operative. However, leaving the sludge in place in a reactor after removing the hydrocarbon phase, the sludge, fortified if necessary with an additional small quantity of fresh $AlCl_3$ can be used for isomerization of subsequent amounts of tetrahydroalkyldienes.

The following examples illustrate embodiments of the present invention.

EXAMPLES

Run 1 was performed in the following manner. Five grams of essentially endo-THDMeDCPD were placed in a 25 milliliter Erlenmeyer flask along with 1.6 grams of anhydrous $AlCl_3$. Properties of the feed tetrahydrodimethyldiene are given in the accompanying Table. The flask and its contents were heated, while stirred, to a temperature of about 33° C when its temperature rose to 59° C and then dropped. Its temperature was then raised to 72° C and then allowed to return to 38° C. At the endo of 8 minutes the stirring was stopped and two layers formed. The hydrocarbon liquid was separated from a brownish sludge phase by decantation and the light clear yellow hydrocarbon was washed with a saturated solution of KCl and water to remove any remaining $AlCl_3$. The resulting water white liquid was then dired and the resulting isomeric tetrahydrodiene mixture tested as to its viscosity, density and pour point. The results are reported in the accompanying Table.

Run 2 was performed in a manner similar to that of Run 1 except that the reaction time was 30 minutes. Samples of the resulting isomeric tetrahydroalkyldiene mixture at the end of Runs 1 and 2 were also examined by vapor phase chromatography (vpc).

Comparison of the properties of the resulting product of Run 1 with the feed clearly show that the undesirable high melt point was substantially reduced after about 8 minutes of isomerization. Further, analysis of the vpc peaks indicated that even after 30 minutes of isomerization no measurable amount of alkyladamantane was formed. The analysis also indicated that the product consisted of only isomeric tetrahydrodienes.

Run 3 was performed in a manner similar to Runs 1 and 2 except for two differences. In Run 3, 15.5 grams of endo-THDMeDCPD, 10.0 grams of methylene dichloride solvent and 2.0 grams of anhydrous AlCl₃ were used. Also in Run 3 the contacting temperature was 0° C and the time of the run was 60 minutes. Surprisingly, even at this low temperature isomerization did occur as shown by the data in the Table. The properties of the resulting product shown in the Table were obtained after boiling off the solvent and the product treated to remove sludge in the manner described previously. The product yield was in excess of 95% and it had a boiling point of about 91°-92° C at 20 mm of Hg. The net heat of combustion for the isomeric mixture is as shown in the Table.

Run 4 was performed in a manner similar to Run 3, except for two differences. In Run 4, ten grams of endo-THDMeDCPD, 7 grams of methylene dichloride solvent and 1.8 grams of anhydrous AlCl₃ were used. Also, the temperature of the run for the first two hours was at 0° C and then it was at about 20° C (room temperature) for ½ additional hours. Properties of the resulting product, which were obtained after boiling off the solvent and treating to remove the sludge etc. in the manner described previously, are as shown in the Table. The product yield was in excess of 95% and it had a boiling point of about 84° at 16 mm of Hg.

Comparison of the pour points of the resulting products with the melting point of the feed clearly indicates the substantial improvement resulting from the increased isomerization time. Further comparison indicate the improvement in viscosity. As the isomerization time increased some decrease in density occurred.

Because of the aforementioned properties the resulting exo-tetrahydroalkyldiene can be used to correct deficiencies in existing missile fuels. Some of the fuels have e.g. too high a pour point, for use at higher and colder altitudes. By diluting the aforementioned missile fuel with some exo-tetrahydroalkyldiene the resulting fuel mixture will have an improved pour point without suffering from a substantial decrease in net heat of combustion.

In a similar manner endo-THMeDCPD can be isomerized to exo-THMeDCPD and the properties of the resulting isomeric mixture are improved in an analogous manner. Also equally similar results can be obtained when an inert solvent such as tetrachloroethane or pentachloroethane are used.

The invention claimed is:
1. Process for isomerizing endo-tetrahydroalkyldicyclopentadienes comprising:
    (a) contacting an endo-tetrahydroalkyldicyclopentadiene selected from the group consisting of endo-tetrahydromethyldicyclopentadiene, endo-tetrahydrodimethyldicyclopentadiene, and a mixture of the foregoing, with anhydrous aluminum trichloride wherein the mole ratio of the trichloride to the endo-tetrahydroalkyldicyclopentadiene is in the range between from about 0.001 to about 0.5 and temperature of the contacting is in the range between from about 0° C to about 100° C;
    (b) continuing contacting until resulting isomeric mixture of tetrahydroalkydiene has a kinematic viscosity and a pour point making it useful as diluent for high energy missile fuel; and
    (c) recovering the isomeric tetrahydroalkydiene.
2. Process according to claim 1 wherein the viscosity is less than about 4 cst.
3. Process according to claim 2 wherein the pour point is less than 0° F.
4. Process according to claim 3 wherein in addition the density is in the range between from about 0.9216 to about 0.9079.
5. Process according to claim 4 wherein the mole ratio of the trichloride to the endo-tetrahydroalkyldicyclopentadiene is in the range between from about 0.01 to about 0.2.
6. Process according to claim 1 wherein an inert solvent is present.
7. Process according to claim 6 wherein the inert solvent is a chlorinated paraffin.
8. Process according to claim 7 wherein the viscosity is less than about 4 cst and the pour point is less than 0° F and the density is in the range between from about 0.9216 to about 0.9079, and the mole ratio of the trichloride to the endo-tetrahydroalkyldicyclopentadiene is in the range between from about 0.01 to about 0.02.
9. Process according to claim 1 wherein sludge, from a previous isomerization of the endo-tetrahydroalkyldicyclopentadiene, fortified with a small quantity of fresh aluminum trichloride is used to contact and isomerize a subsequent amount of endo-tetrahydroalkyldicyclopentadiene.

* * * * *

TABLE

PROPERTIES OF TETRAHYDRODIMETHYLDICYCLOPENTADIENES**

| Run | Solvent | Reaction Time | Reaction Temperature °C | Density ($\frac{20}{4}$ °C) | Kinematic Viscosity at 100° F, cst. | Pour Point | Net Heat of Combustion, BTU/lb |
|---|---|---|---|---|---|---|---|
| Feed | n.a. | n.a. | n.a. | 0.9216 | 4.01 | 0° F m.p. | 18,480 |
| 1 | None | 8 min | 33–38° C* | 0.9177 | 3.61 | −100° F | — |
| 2 | None | 30 min | 33–43° C* | 0.9126 | 3.20 | −100° F | — |
| 3 | CH₂Cl₂ | 60 min | 0° C | 0.9111 | 3.12 | — | 18,420 |
| 4 | CH₂Cl₂ | 2 hrs. & 2.5 hrs. | 0° C 20° C | 0.9079 | 2.78 | −100° F | 18,280 |

*See Examples for additional information as to temperatures.
**Formula, C₁₂H₂₀, C/H atomic ratio = 0.6.
n.a. = not applicable